United States Patent [19]

Kummer et al.

[11] Patent Number: 5,189,182

[45] Date of Patent: Feb. 23, 1993

[54] PREPARATION OF 5-METHYLBUTYROLACTONE

[75] Inventors: Rudolf Kummer, Frankenthal; Heinz-Walter Schneider, Ludwigshafen; Werner Bertleff, Viernheim; Rolf Fischer, Heidelberg; Uwe Vagt, Speyer; Fritz Naeumann, Mannheim; Wolfgang Hoelderich, Frankenthal; Matthias Schwarzmann, Limburgerhof, all of Fed. Rep. of Germany

[73] Assignee: BASF Aktiengesellschaft, Ludwigshafen, Fed. Rep. of Germany

[21] Appl. No.: 236,199

[22] Filed: Aug. 25, 1988

[30] Foreign Application Priority Data

Sep. 9, 1987 [DE] Fed. Rep. of Germany ....... 3730186
Feb. 2, 1988 [DE] Fed. Rep. of Germany ....... 3802980

[51] Int. Cl.$^5$ .......................................... C07D 307/20
[52] U.S. Cl. .................................. 549/326; 549/295
[58] Field of Search .............................. 549/326, 295

[56] References Cited

U.S. PATENT DOCUMENTS

| 2,420,250 | 6/1947 | Kyrides | 549/295 |
| 2,509,859 | 5/1950 | Coffman et al. | 549/295 |
| 3,037,052 | 5/1962 | Bortnick | 549/295 |
| 3,786,069 | 1/1974 | Aviron-Violet | 549/295 |
| 3,944,572 | 3/1976 | King et al. | 260/343.6 |
| 4,310,440 | 1/1982 | Wilson et al. | 423/305 |
| 4,380,650 | 1/1983 | Coleman et al. | 549/326 |
| 4,420,622 | 12/1983 | van der Moesdijk et al. | 549/366 |
| 4,740,613 | 4/1988 | Fisher et al. | 560/205 |
| 4,853,473 | 8/1989 | Fisher et al. | 549/326 |

FOREIGN PATENT DOCUMENTS

| 69409 | 11/1985 | European Pat. Off. |
| 238003 | 3/1987 | European Pat. Off. |
| 896343 | 10/1953 | Fed. Rep. of Germany |
| 2122501 | 11/1971 | Fed. Rep. of Germany |

OTHER PUBLICATIONS

M. Ansell et al. *Journal of the Chemical Society*, pp. 2640-2644 (1963).

J. Mackenzie, *Annalen des Chemie*, 283, pp. 82-100 (1894).
E. J. Boorman, *Journal of the Chemical Society*, pp. 577-585 (1933).
R. Morrison, et al., "Organic Chemistry" 3rd ed. pp. 155, 191 & 674, Allyn and Bacon, Inc., Boston (1973).
J. March, "Advanced Organic Chemistry" 2nd ed., p. 366, McGraw-Hill Co., New York (1977).
*Chemical Abstracts*, 97:100745t, "Electro preparation of n-valenionic acid and its Esters," (1982).
*Merck Index*, 10th ed., 9922, p. 1454 (1983).

*Primary Examiner*—Richard L. Raymond
*Assistant Examiner*—Mark W. Russell
*Attorney, Agent, or Firm*—Keil & Weinkauf

[57] ABSTRACT

5-Methylbutyrolactone is prepared by a process in which a pentenoic ester of the formula I $$X-CO_2R \quad (I),$$

where X is $CH_2=CH-CH_2-CH_2-$, $CH_3-CH=CH-CH_2-$ or $CH_3-CH_2-CH=CH-$ and R is alkyl, cycloalkyl, aralkyl or aryl, or a mixture of these esters is reacted with water at from 50° to 350° C. in the presence or absence of a diluent
a) over a zeolite and/or phosphate catalyst or
b) in the presence of from 0.01 to 0.25 mole of a sulfonic acid, a Lewis acid and/or a non-oxidizing mineral acid per mole of pentenoic ester or over from 0.1 to 40% by weight, based on the pentenoic ester, of a strongly acidic ion exchanger as a catalyst in a first stage, or the pentenoic ester of the formula I, where X and R have the stated meanings, is hydrolyzed in a first stage with the aid of a strongly acidic ion exchanger as a catalyst to give the pentenoic acid of the formula I, where R is hydrogen, and the resulting pentenoic acid is subjected to cyclization in a second stage in the presence of from 0.005 to 0.1 mole of a sulfonic acid, a Lewis acid or a non-oxidizing mineral acid per mole of pentenoic acid or over from 0.1 to 20% by weight, based on the pentenoic acid, of a strongly acidic ion exchanger at from 50° to 350° C.

9 Claims, No Drawings

PREPARATION OF 5-METHYLBUTYROLACTONE

The present invention relates to a process for the preparation of 5-methylbutyrolactone by reacting a pentenoic ester with water in the presence of an aicidic catalyst.

U.S. Pat. No. 2,509,859 and DE 896,343 disclose that 5-methylbutyrolactone is formed by cyclization of pentenenitriles with non-oxidizing mineral acids, such as hydrochloric acid or sulfuric acid. However, this method has the disadvantage that equimolar amounts of ammonium salts are inevitably produced.

Furthermore, according to a large number of publications, 5-methylbutyrolactone can also be prepared by reducing levulinic acid or its esters (for example with sodium amalgam, complex hydrides, such as lithium borohydride, or hydrogen in the presence of a suitable hydrogenation catalyst). For example, European Patent 069,409 describes the hydrogenation of levulinic esters with hydrogen over Ni/Co catalysts.

Furthermore, 5-methylbutyrolactone can be prepared, according to U.S. Pat. No. 2,420,250, by cyclization of 1,4-pentanediol over copper/chromite catalysts under dehydrogenating conditions or, according to German Laid-Open Application DOS 2,122,501, by isomerization of δ-valerolactone over boric acid/phosphoric acid catalysts.

The stated methods are not very suitable for an industrial process since the starting materials are on the one hand expensive and on the other hand not available in appropriately large amounts.

It is also known that pentenoic acids can be subjected to cyclization with sulfuric acid to give 5-methylbutyrolactone. For example, J. Chem. Soc. 1963, 2640-2644 describes the cyclization of 4-, 3-trans- and 2-trans-pentenoic acid with 50% sulfuric acid. The resulting yields of 5-methylbutyrolactone, which are almost 50%, are, however, very unsatisfactory. Moreover, this procedure and all earlier procedures (such as Liebigs Annalen 283 (1984), 86 and J. Chem. Soc. 1933, 577–586) employ uneconomically large amounts of sulfuric acid (about 10 g of sulfuric acid per g of pentenoic acid). Moreover, because of this the lactone is isolated from the reaction mixtures by a very expensive process, for example by steam distillation.

It is an object of the present invention to provide processes which start from readily available starting materials and give 5-methylbutyrolactone in good yields.

We have found that this object is achieved, according to the invention, by a process for the preparation of 5-methylbutyrolactone, wherein a pentenoic ester of the formula $$X-CO_2R \quad (I),$$

where X is $CH_2=CH-CH_2-CH_2-$, $CH_3-CH=CH-CH_2-$ or $CH_3-CH_2-CH=CH-$ and R is alkyl, cycloalkyl, aralkyl or aryl, or a mixture of these esters is reacted with water at from 50° to 350° C. in the presence or absence of a diluent a) over a zeolite and/or phosphate catalyst or
b) in the presence of from 0.01 to 0.25 mole of a sulfonic acid, a Lewis acid and/or a non-oxidizing mineral acid per mole of pentenoic ester or over from 0.1 to 40% by weight, based on the pentenoic ester, of a strongly acidic ion exchanger as a catalyst in a first stage, or the pentenoic ester of the formula I, where X and R have the stated meanings, is hydrolyzed in a first stage with the aid of a strongly acidic ion exchanger as a catalyst to give the pentenoic acid of the formula I, where R is hydrogen, and the resulting pentenoic acid is subjected to cyclization in a second stage in the presence of from 0.005 to 0.1 mole of a sulfonic acid, a Lewis acid or a non-oxidizing mineral acid per mole of pentenoic acid or over from 0.1 to 20% by weight, based on the pentenoic acid, of a strongly acidic ion exchanger at from 50° to 350° C.

For example for the conversion of methyl 2-trans-pentenoate to 5-methylbutyrolactone, the reaction according to the invention can be represented by the following equation:

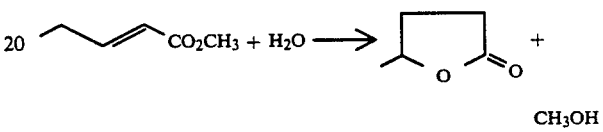

CH₃OH

The esters of the formula I which are required as starting materials are, in particular, $C_1-C_{12}$-alkyl, $C_5-C_{10}$-cycloalkyl, in particular $C_5$- and $C_6$-cycloalkyl, $C_7-C_{15}$-aralkyl and $C_6-C_{10}$-aryl esters of the corresponding acids, such as 4-pentenoic acid, 3-cis- or 3-trans-pentenoic acid or 2-trans- or 2-cis-pentenoic acid. Examples of radicals R are methyl, ethyl, propyl, isopropyl, n-butyl, isobutyl, sec-butyl, tert-butyl, hexyl, nonyl, dodecyl, cyclopentyl, cyclohexyl, phenyl and benzyl radicals, which may be further substituted in the alcohol component, for example by $C_1-C_4$-alkyl, $C_1-C_4$-alkoxy or halogen, such as fluorine, chlorine, bromine or iodine. Particularly preferred starting materials of the formula I are $C_1-C_6$-alkyl pentenoates.

For example, the following pentenoic esters of the formula I or mixtures of these are suitable starting materials: methyl 4-pentenoate, methyl 3-trans-pentenoate, methyl 3-cis-pentenoate, methyl 2-trans-pentenoate, methyl 2-cis-pentenoate, ethyl 4-pentenoate, ethyl 3-trans-pentenoate, ethyl 3-cis-pentenoate, ethyl 2-trans-pentenoate, ethyl 2-cis-pentenoate, propyl 4-pentenoate, propyl 3-trans-pentenoate, propyl 3-cis-pentenoate, propyl 2-trans-pentenoate, propyl 2-cis-pentenoate, butyl 4-pentenoate, butyl 3-trans-pentenoate, butyl 3-cis-pentenoate, butyl 2-trans-pentenoate, butyl 2-cis-pentenoate, hexyl 4-pentenoate, nonyl 3-trans-pentenoate, dodecyl 3-cis-pentenoate, cyclopentyl 2-trans-pentenoate, cyclohexyl 2-cis-pentenoate, benzyl 4-pentenoate, benzyl 3-trans-pentenoate, phenyl 3-cis-pentenoate, phenyl 2-trans-pentenate and phenyl 2-cis-pentenoate.

The reaction is carried out at from 50° to 350° C., preferably from 80° to 260° C., in general under atmospheric pressure. However, it is also possible to employ slightly reduced or superatmospheric pressure of from 0.01 to 50 bar.

The reaction is carried out in the presence of water. In general, from 0.2 to 30, in particular from 0.5 to 20, particularly preferably from 1 to 10, moles of water are used per mole of pentenoic ester of the formula I.

The catalysts used for the novel process are a) zeolites and/or phosphates.

Zeolites are crystalline aluminum silicates which have a highly ordered structure with a rigid three-dimensional network of SiO$_4$ and AlO$_4$ tetrahedra which are bonded by common oxygen atoms. The ratio of Si and Al atoms to oxygen is 1:2. The electrovalency of the aluminum-containing tetrahedra is balanced by the inclusion of cations in the crystal, for example an alkali metal ion or hydrogen ion. Cation exchange is possible. The voids between the tetrahedra are occupied by water molecules prior to dehydration by drying or calcination.

In the zeolites, other elements such as B, Ga, Fe, Cr, V, As, Sb, Bi or Be, or mixtures of these can be incorporated in the framework instead of aluminum, or the silicon can be replaced by a tetravalent element, such as Ge, Ti, Zr or Hf.

Depending on their structure, zeolites are divided into different groups. For example, the zeolite structure is formed by chains of tetrahedra in the mordenite group and by sheets of tetrahedra in the chabasite group, while in the faujasite group the tetrahedra are arranged to form polyhedra, for example in the form of a cubooctahedron, which is composed of 4-membered rings and 6-membered rings. Depending on the bonding of the cubooctahedra, which gives rise to cavities and pores of different sizes, a distinction is made between zeolites of type A, L, X and Y.

Catalysts which are suitable for the novel process are zeolites from the mordenite group or narrow-pore zeolites of the erionite or chabasite type or zeolites of the faujasite type, for example Y, X or L zeolites. This group of zeolites includes the ultrastable zeolites of the faujasite type, i.e. dealuminated zeolites. Processes for the preparation of such zeolites are described in, for example, Catalysis by Zeolites, Volume 5, from Studies in Surface Science and Catalysis, ed. B. Imelik et al., Elsevier Scientific Publishing Company, 1980, page 203, and Crystal Structures of Ultra-stable Faujasites, Advances in Chemistry, Series No. 101, Americal Chemical Society, Washington, D.C., page 226 et seq (1971) and in U.S. Pat. No. 4,512,961.

Zeolites of the pentasil type are particularly advantageous. These have a 5-membered ring consisting of SiO$_4$ tetrahedra as a common building block. They have a high SiO$_2$/Al$_2$O$_3$ ratio and pore sizes which are between those of the zeolites of type A and those of type X or Y (cf. Ullmanns Encyclopädie d. techn. Chem., 4th Edition, Vol. 24, 1983).

These zeolites may have different chemical compositions. They are aluminosilicate, borosilicate, iron silicate, beryllium silicate, gallium silicate, chromium silicate, arsenosilicate, antimony silicate and bismuth silicate zeolites or mixtures of these, and aluminogermanate, borogermanate, gallium germanate and iron germanate zeolites or mixtures of these. The aluminosilicate, borosilicate and iron silicate zeolites of the pentasil type are particularly suitable for the novel process.

The aluminosilicate zeolite is prepared, for example, from an aluminum compound, preferable Al (OH)$_3$ or Al$_2$(SO$_4$)$_3$, and a silicon component, preferably finely divided silica, in aqueous amine solution, in particular in a polyamine, such as 1,6-hexanediamine, 1,3-propanediamine or triethylenetetramine solution, with or, in particular, without the addition of an alkali or alkaline earth, at from 100° to 220° C. under autogenous pressure. They also include the isotactic zeolites according to European Patents 34,727 and 46,504. The aluminosilicate zeolites obtained have an SiO$_2$/Al$_2$O$_3$ ratio of from 10 to 40,000, depending on the amounts of starting materials. Such aluminosilicate zeolites can also be synthesized in an ether medium, such as diethylene glycol dimethyl ether, in an alcoholic medium, such as methanol or 1,4-butanediol, or in water.

The borosilicate zeolite is synthesized, for example, at from 90° to 200° C. under autogenous pressure by reacting a boron compound, e.g. H$_3$BO$_3$, with a silicon compound, preferably finely divided silica, in aqueous amine solution, in particular in 1,6-hexanediamine or 1,3-propanediamine or triethylenetetramine solution, with or, in particular, without the addition of an alkali or alkaline earth. These zeolites also include the isotactic zeolites according to European Patents 34,727 and 46,504. Such borosilicate zeolites can also be prepared if the reaction is carried out in solution in ether solution, e.g. diethylene glycol dimethyl ether, or in alcohol solution, e.g. 1,6-hexanediol, instead of in aqueous amine solution.

The iron silicate zeolite is obtained, for example, from an iron compound, preferably Fe$_2$(SO$_4$)$_3$, and a silicon compound, preferably finely divided silica, in aqueous amine solution, in particular 1,6-hexanediamine, with or without the addition of an alkali or alkaline earth, at from 100° to 220° C. under autogenous pressure.

The aluminosilicate, borosilicate and iron silicate zeolites thus prepared can be isolated, dried at from 100° to 160° C., preferably 110° C. and calcined at from 450° to 550° C., preferably 500° C., and then molded with a binder in a weight ratio of from 90:10 to 40:60 to give extrudates or pellets. Suitable binders are various aluminas, preferably boehmite, amorphous aluminosilicates having an SiO$_2$/Al$_2$O$_3$ ratio of from 25:75 to 95:5, preferably 75:25, silica, preferably finely divided SiO$_2$, mixtures of finely divided SiO$_2$ and finely divided Al$_2$O$_3$, TiO$_2$, ZrO$_2$ and clay. After the molding procedure, the extrudates or pellets are dried at 110° C. for 16 hours and calcined at 500° C. for 16 hours.

Advantageous catalysts are also obtained if the aluminosilicate or borosilicate zeolite isolated is molded directly after drying and is not calcined until after the molding procedure. The aluminosilicate and borosilicate zeolites prepared can be used in pure form, without a binder, as extrudates or pellets, examples of extrusion assistants or peptizing assistants used being ethylcellulose, stearic acid, potato starch, formic acid, oxalic acid, acetic acid, nitric acid, ammonia, amines, silicoesters and graphite or mixtures of these.

The silicon-rich zeolites which can be used according to the invention (SiO$_2$/Al$_2$O$_3 \geq$ 10) include the various ZSM types: ZSM-5 (U.S. Pat. Nos. 3,702,886, 3,832,449 and 4,076,859), ferrierite (European Patent 12,473), Nu-1 (U.S. Pat. No. 4,060,590) and Silicalit ® (U.S. Pat. No. 4,061,724).

Silicalits ® can be prepared, for example, from silica sols in the presence of tetrapropylammonium hydroxide and in the presence or absence of an alkali metal hydroxide under hydrothermal conditions at from 150° to 250° C. The Silicalit ® powders thus prepared can be isolated, dried at from 100° to 160° C., preferably 110° C., and calcined at from 350° to 550° C., preferably from 450° to 500° C., and then molded with a binder in a weight ratio or from 90:10 to 20:80 to give extrudates or pellets or fluidizable material. Suitable binders are various aluminas, preferably boehmite, amorphous aluminosilicates having an SiO$_2$/Al$_2$O$_3$ ratio of from 25:75 to 95:5, preferably 75:25, silica, preferably finely divided SiO$_2$, and finely divided Al$_2$O$_3$, TiO$_2$, ZrO$_2$ and clay. After the molding procedure, the extrudates or pellets are dried at 110° C. for 16 hours and calcined at 500° C. for 16 hours.

If, because of its method of preparation, the zeolite is, for example, in the Na form, the latter can be completely or partially converted into the H form by ion exchange, for example with ammonium ions, and subsequent calcination or by treatment with acids.

It may also be advantageous to modify the zeolites. In a suitable method of modifying the catalysts, for example, the unmolded or molded zeolites are doped with metal salts by ion exchange or by impregnation. Suitable metals are alkali metals, such as Li, Cs or K, alkaline earth metals, such as Mg, Ca, Sr or Ba, metals of main groups 3, 4 and 5, such as B, Al, Ga, Ge, Sn, Pb or Bi, or transition metals.

This doping is advantageously carried out by initially taking the molded zeolites in a riser tube and passing an aqueous or ammoniacal solution of a halide or of a nitrate of the metals described above over the said zeolites at from 20° to 100° C. Ion exchange of this type can be carried out on the hydrogen, ammonium and alkali metal form of the zeolite. In another possible method of applying metals to the zeolites, the zeolite material is impregnated, for example with a halide, a nitrate or an oxide of the metals described above in aqueous, alcoholic or ammoniacal solution. Both ion exchange and impregnation are followed by one or more drying procedures and, if desired, repeated calcination.

The zeolite in the H form or ammonium form or alkali metal form can be subjected to ion exchange by a method in which the zeolite, in the form of extrudates or pellets, is initially taken in a column and a solution of the metal salt is circulated over the said zeolite for from 15 to 20 hours at slightly elevated temperatures of from 30° to 80° C. The product is then washed thoroughly with water, dried at about 150° C. and calcined at about 550° C.

Other catalysts for the novel process are phosphates, in particular aluminum phosphates, silicon aluminum phosphates, boron aluminum phosphates, silicon iron aluminum phosphates, cerium phosphates, zirconium phosphates, boron phosphates, iron phosphates, strontium phosphate or mixtures of these.

Suitable aluminum phosphate catalysts for the novel process are, in particular, aluminum phosphates synthesized under hydrothermal conditions.

The aluminum phosphates (APO) prepared under hydrothermal conditions are, for example, APO-5, APO-9, APO-11, APO-12, APO-14, APO-21, APO-25, APO-31 and APO-33. Syntheses of these compounds are described in European Patent 132,708, U.S. Pat. No. 4,310,440 and U.S. Pat. No. 4,473,663 or by S. T. Wilson, B. M. Lok, C. A. Messina and E. M. Flanigen in Proc. 6th Fut. Zeolite Conf., Reno 1983, ed. D. M. Olson and A. Bisio, pages 97-109.

For example, $AlPO_4$-5 (APO-5) is synthesized by mixing orthophosphoric acid with pseudoboehmite (Catapal SB ®) in water to give a homogeneous mixture; tetrapropyl ammonium hydroxide is added to this mixture, after which the reaction is carried out at about 150° C. for from 20 to 60 hours under autogenous pressure in an autoclave. The $AlPO_4$ filtered off is dried at from 100° to 160° C. and calcined at from 450° to 550° C.

$AlPO_4$-9 (APO-9) is likewise synthesized from orthophosphoric acid and pseudoboehmite, but in aqueous 1,4-diazabicyclo[2.2.2]octane solution (DABCO solution) at about 200° C. under autogenous pressure in the course of from 200 to 400 hours. If ethylenediamine is used instead of DABCO solution, APO-12 is obtained.

$AlPO_4$-21 (APO-21) is synthesized from orthophosphoric acid and pseudoboehmite in aqueous pyrrolidone solution at from 150° to 200° C. under autogenous pressure in the course of from 50 to 200 hours.

The silicon aluminum phosphates (SAPO) which can be used for the novel process are, for example, SAPO-5, SAPO-11, SAPO-31 and SAPO-34. The synthesis of these compounds is described, for example, in European Patent 103,117 or U.S. Pat. No. 4,440,871 or by E. M. Flanigen et al. in Pure Appl. Chem. 58 (1986), 1351-1358. Silicon aluminum phosphates are prepared by crystallization from an aqueous mixture at from 100° to 250° C. and under autogenous pressure in the course of from 2 hours to 2 weeks, the reaction mixture of a silicon, aluminum and phosphorus component being reacted in an aqueous solution containing an organic amine.

For example, SAPO-5 is obtained by mixing $SiO_2$, suspended in aqueous tetrapropylammonium hydroxide solution, with an aqueous suspension of pseudoboehmite and orthophosphoric acid and then carrying out the reaction at from 150° to 200° C. in the course of from 20 to 200 hours under autogenous pressure in a stirred autoclave. The powder filtered off is dried at from 110° to 160° C. and calcined at from 450° to 550° C.

Other suitable silicon aluminum phosphates are ZYT-5, ZYT-6, ZYT-7, ZYT-9, ZYT-11 and ZYT-12. Such silicon aluminum phosphates are described, for example, in Japanese Patent Application 59217-619/1984.

Boron phosphates for the novel process can be prepared, for example, by mixing and kneading concentrated boric acid and phosphoric acid and by subsequent drying and calcination in an inert gas, air or steam atmosphere at from 250° to 650° C., preferably from 300° to 500° C.

Precipitated aluminum phosphates can also be used as phosphate catalysts in the process. For example, an aluminum phosphate of this type is prepared by dissolving 92 g of diammonium hydrogen phosphate in 700 ml of water. 260 g of $Al(NO_3)_3 \cdot H_2O$ in 700 ml of water are added dropwise to this solution in the course of 2 hours. During this procedure, the pH is kept at 8 by simultaneous addition of 25% strength $NH_3$ solution. The resulting precipitate is stirred for a further 12 hours and then filtered off under suction and washed thoroughly. It is dried at 60° C. for 16 hours.

Modifying components, as described above in the case of the zeolites, can be applied to these phosphates by impregnation (immersion and spraying) or in some cases also by ion exchange. Modification can also be effected using acids, for example phosphoric acid, as in the case of the zeolite catalysts.

The catalysts described here can alternatively be used as 2-4 mm extrudates or as tablets having a diameter of from 3 to 5 mm or as chips having particle sizes of from 0.1 to 0.5 mm or as a fluidizable catalyst.

The catalysts used according to the invention for the preparation of 5-methylbutyrolactone show no loss of activity even over a prolonged period, particularly when the reaction is carried out in an alcohol. If, when the zeolite catalysts or the other catalysts suitable for this purpose are used according to the invention, deactivation occurs as a result of coking, it is advisable to regenerate these catalysts by burning off the coke deposit with air or with an air/$N_2$ mixture at from 400° to 550° C., preferably 500° C. As a result, the catalysts regain their initial activity.

By precoking, it is possible to adjust the activity of the catalyst to achieve optimum selectivity with respect to the desired reaction product.

The space velocity is in general from 0.01 to 40, preferably from 0.1 to 20, kg of pentenoic ester I per kg of catalyst per hour.

The reaction can be carried out batchwise or continuously, as a fixed-bed reaction using fixed-bed catalysts, for example by the liquid phase or trickle-bed procedure, in the liquid or gas phase, or as a fluidized-bed reaction with catalysts fluidized upward and downward, in the gas phase, or in the liquid phase using homogeneous catalysts or suspended fixed-bed catalysts.

The yield, the selectivity and the catalyst life can also be advantageously influenced if the reaction is carried out in the presence of diluents. Examples of suitable diluents are alcohols of 1 to 6 carbon atoms or cyclohexanol, ethers, such as dioxane or tetrahydrofuran, chlorohydrocarbons, eg. methylene chloride, chloroform or 1,2-dichloroethane, aliphatic, cycloaliphatic or aromatic hydrocarbons, such as benzene, toluene, cyclohexane or paraffins. From 0.2 to 50, in particular from 0.5 to 20, moles of solvent are used per mole of pentenoic ester I. Particularly preferred diluents are alcohols.

In a possible advantageous embodiment of the novel process in the gas phase, for example, a mixture of pentenoic ester I and, if required, a diluent is vaporized and then passed, together with steam and, if required, a carrier gas, such as nitrogen, carbon dioxide or argon, at the desired reaction temperature in gaseous form into a fixed or fluidized catalyst bed, the reacted mixture is condensed and the organic phase is separated off and then worked up by fractional distillation. Unconverted pentenoic ester I can be recycled.

The catalysts used under b) are sulfonic acids, for example p-toluenesulfonic acid or benzenesulfonic acid, Lewis acids, such as boron trifluoride or zinc chloride, non-oxidizing mineral acids, such as sulfuric acid or phosphoric acid, and strongly acidic cation exchangers, for example those consisting of crosslinked polystyrene having sulfo groups or phenol resins having sulfo groups. Cation exchangers of this type are described in detail in HOUBEN-WEYL, Methoden der org. Chemie, Vol. I/1, page 528 et seq, which is herewith incorporated by reference. Lewis acids are the acidic halides of the elements of main groups III, IV and V of the Periodic Table of Elements and of the subgroup elements. These are, for example, aluminum chloride, boron trifluoride, silicon tetrachloride, antimony pentachloride, tin tetrachloride, zinc chloride, titanium tetrachloride and iron(III) chloride.

The reaction can be carried out in the gas phase or in the liquid phase, the latter being preferred.

The single-stage reaction can be carried out batchwise or continuously as a fixed-bed reaction with fixed-bed catalysts, for example by the liquid phase or trickle-bed procedure in the liquid or gas phase, or using catalysts suspended or dissolved in the liquid phase.

The sulfonic acids, Lewis acids and/or nonoxidizing mineral acids used as catalysts are required only in catalytic amounts, for example from 0.01 to 0.25, in particular from 0.05 to 0.15, mole per mole of pentenoic ester. The strongly acidic cation exchangers are used in general in amounts of from 0.1 to 40, in particular from 1 to 20, % by weight based on the pentenoic ester used, in the batchwise procedure. In the continuous procedure, a throughput of from 0.1 to 10 g of methyl pentenoate per g of strongly acidic cation exchanger is advantageously chosen.

The preferred reaction in the liquid phase is carried out, for example, as follows: a mixture of the ester and water is heated in the presence of a suspended or dissolved catalyst, and the alcohol formed is distilled off continuously. Particularly advantageously, the major part of the water is added to the reaction mixture only at the rate at which the alcohol is distilled off. After the necessary reaction time, the reaction mixture is distilled in order to obtain the 5-methylbutryolactone. Unconverted ester is obtained as first runnings and can be recycled.

In another version of the novel process, which version is particularly advantageous in many cases, a two-stage reaction procedure is chosen. In this procedure, A) the pentenoic ester of the formula I is first hydrolyzed with water at from 30° to 200° C. in the presence of an acidic cation exchanger, if necessary with simultaneous removal of the alcohol formed, to give the pentenoic acid (stage A) and B) the ion exchanger is separated off by filtration and, if necessary, the pentenoic acid is isolated, for example by distillation or extraction, after which the pentenoic acid is subjected to cyclization at from 50° to 350° C. in the presence of an acidic agent to give 5-methylbutyrolactone (stage B).

In general, from 1 to 200, in particular from 50 to 150, moles of water are used per mole of pentenoic ester in the hydrolysis (stage A).

The hydrolysis is generally carried out at from 30° to 200° C. Advantageously, temperatures of from 50° to 120° C. are employed and the hydrolysis is carried out under atmospheric pressure. However, it is also possible to use slightly reduced or superatmospheric pressure, for example up to 20 bar.

The strongly acidic cation exchangers used are of the same type are those described for the single-stage procedure.

The hydrolysis can be carried out batchwise or, advantageously, continuously, for example in a cascade of stirred kettles. In this procedure, it is advantageous if the alcohol formed in the hydrolysis is removed continuously from the reaction mixture by distillation. In the batchwise procedure, in general from 1 to 40, in particular from 5 to 30, % by weight, based on the pentenoic ester used, of strongly acidic cation exchanger are employed. In the continuous procedure, a throughput of from 0.1 to 10 g of methyl pentenoate per g of strongly acidic cation exchanger is advantageously chosen.

The product of the hydrolysis is a mixture of the pentenoic acid with the excess water. The pentenoic acid can be obtained in pure form from this mixture by distillation or extraction, for example with an ether, such as methyl tert-butyl ether. However, it is also possible for the pentenoic acids obtained after the hydrolysis to be cyclized directly, i.e. without isolation, in the aqueous solutions.

The cyclization (stage B) is carried out at from 50° to 350° C., preferably from 90° to 250° C., in general under atmospheric pressure; however, it is also possible to employ slightly reduced or superatmospheric pressure, for example up to 50 bar.

Suitable catalysts for the cyclization are the same acidic catalysts as those stated for the single-stage reaction. The cyclization of the pentenoic acid can be carried out in the gas phase or in the liquid phase, the reaction being preferably carried out in the liquid phase.

The reaction can be carried out batchwise or continuously, as a fixed-bed reaction using fixed-bed catalysts, for example by the liquid phase or trickle-bed procedure, in the liquid or gas phase, or using catalysts suspended or dissolved in the liquid phase.

The sulfonic acids, Lewis acids and/or nonoxidizing mineral acids are required only in catalytic amounts, for example in amounts of from 0.002 to 0.25, in particular from 0.005 to 0.1 mole per mole of pentenoic ester. In the batchwise procedure, the strongly acidic cation exchangers are used in general in amounts of from 0.1 to 20, in particular from 0.5 to 15, % by weight, based on the pentenoic ester used. In the continuous procedure, a throughput of from 0.1 to 10 g of pentenoic acid per g of strongly acidic cation exchanger is advantageously chosen.

The preferred reaction in the liquid phase is carried out, for example, by heating the pentenoic acid in the presence of a suspended or dissolved catalyst. After the necessary reaction time, which as a rule is from 0.1 to 1 hour, the reaction mixture is distilled in order to obtain the 5-methylbutyrolactone.

Compared with the known process, the novel process for the preparation of 5-methylbutyrolactone has the advantage that the product is obtained in a simple manner in excellent yield from readily available starting materials.

The pentenoic esters can in fact be prepared readily and in high yields by carbonylation of butadiene in the presence of alcohols or by elimination of water or hydrogen halide from hydroxy- or halovalerates.

The 5-methylbutyrolactone obtainable by the novel process is a useful intermediate, inter alia for the preparation of pyrrolidones, such as 5-methylpyrrolidones, and of pharmaceutical active compounds and active ingredients for crop protection.

The Examples which follow illustrate the process according to the invention.

a) Examples of the use of Zeolites and Phosphates as Catalysts

The reaction was carried out in the gas phase under isothermal conditions in a tube reactor (coil, 0.6 cm internal diameter, 90 cm length) for not less than 6 hours. The gaseous reacted mixtures were condensed in cold traps, the phases were separated and weighed and the reaction products were isolated and characterized by conventional methods. Quantitative determination of the reaction products and of the starting materials was carried out by gas chromatography.

The catalysts used for the novel process are the following:

CATALYST A

An aluminosilicate zeolite of the pentasil type was prepared under hydrothermal conditions, under autogenous pressure and at 150° C., from 65 g of finely divided $SiO_2$ and 20.3 g of $Al_2(SO_4)_3 \cdot 18H_2O$ in 1 kg of an aqueous 1,6-hexanediamine solution (weight ratio 50:50) in a stirred autoclave. The crystalline reaction product was filtered off, washed thoroughly, dried at 110° C. for 24 hours and calcined at 500° C. for 24 hours. This aluminosilicate zeolite contained 91.6% by weight of $SiO_2$ and 4.6% by weight of $Al_2O_3$. The catalyst was molded to give 2 mm extrudates, which were dried at 110° C. for 16 hours and calcined at 500° C. for 24 hours.

CATALYST B

Commercial Na-Y zeolite was subjected to ion exchange with aqueous $(NH_4)_2SO_4$ solution by a known method, until the Na content was about 0.06% by weight (after drying at 110° C. for 2 hours and calcination at 570° C. for 3 hours). The powder thus obtained was molded with molding assistants to give extrudates, which were dried at 110° C. and calcined for 16 hours at 500° C.

CATALYST C

Boron phosphate was prepared by combining 49 g of $H_3BO_3$ with 117 g of 75% strength $H_3PO_4$ in a kneader, evaporating off excess water and molding the reaction product to give 3 mm extrudates. These extrudates were dried at 100° C. and calcined at 350° C. Catalyst G contained 8.77% by weight of B and 28.3% by weight of P.

EXAMPLE 1

About 10 ml/hour of methyl 3-pentenoate and 10 ml/hour of water were vaporized and passed over 3.5 g of catalyst A at 180° C. After the mixture had been condensed, the organic phase was isolated and analyzed by gas chromatography. Analysis gave the following composition:

| | |
|---|---|
| 5-methylbutyrolactone | 24.8% |
| methyl 4-pentenoate | 3.5% |
| methyl 3-pentenoate | 69.8% |
| methyl 2-pentenoate | 1.2% |

EXAMPLE 2

About 10 ml/hour of methyl 3-pentenoate and 10 ml/hour of water were vaporized and passed over 3.5 g of catalyst B at 180° C. The mixture was condensed and the organic phase was isolated and analyzed by gas chromatography:

| | |
|---|---|
| 5-methylbutyrolactone | 47.4% |
| methyl 4-pentenoate | 2.8% |
| methyl 3-pentenoate | 46.0% |
| methyl 2-pentenoate | 2.1% |

EXAMPLE 3

About 10 ml/hour of methyl 3-pentenoate and 10 ml/hour of a mixture of methanol and water (molar ratio 1:1) were vaporized and passed over 3.5 g of catalyst B at 180° C. After the mixture had been condensed, the organic phase was isolated and analyzed by gas chromatography:

| | |
|---|---|
| 5-methylbutyrolactone | 23.3% |
| methyl 4-pentenoate | 8.1% |
| methyl 3-pentenoate | 64.6% |
| methyl 2-pentenoate | 2.7% |

EXAMPLE 4

About 10 ml/hour of methyl 3-pentenoate and 10 ml/hour of water were vaporized and passed over 3.5 g of catalyst C at 250° C. After the mixture had been condensed, the organic phase was isolated and analyzed by gas chromatography:

| | |
|---|---|
| 5-methylbutyrolactone | 22.1% |
| methyl 4-pentenoate | 3.7% |
| methyl 3-pentenoate | 71.7% |
| methyl 2-pentenoate | 1.6% | b) Examples of Acids as Catalysts

EXAMPLE 5

228 g (2.0 moles) of methyl 4-pentenoate, 9 g (0.5 mole) of water and 24 g of concentrated sulfuric acid (11.7 mol %, based on pentenoic ester) were initially taken in a 0.5 l three-necked flask having a 50 cm packed column and were heated at the boil (about 120°–130° C.). Thereafter, the remaining water (27 g, 1.5 moles) was added in the course of 1 hour, the methanol formed during the reaction being distilled off continuously. After all the methanol had been distilled off, the reaction mixture was distilled over a short Vigreux column. 167 g (84% of theory) of pure 5-methylbutyrolactone of boiling point 65°–67° C./10 mbar were obtained.

EXAMPLE 6

228 g (2.0 moles) of methyl 3-pentenoate (cis/trans isomer mixture; about 70% of methyl 3-transpentenoate and 30% of methyl 3-cis-pentenoate), 9 g (0.5 mole) of water and 24 g of concentrated sulfuric acid (11.7 mol %, based on pentenoic ester) were initially taken in a 0.5 l three-necked flask having a 50 cm packed column and were heated at the boil (about 120°–130° C.). Thereafter, the remaining water (27 g, 1.5 moles) was added in the course of 3 hours, the methanol formed during the reaction being distilled off continuously. After all the methanol had been distilled off, the mixture was stirred for a further hour at a bottom temperature of 200° C., after which the reaction mixture was distilled over a short Vigreux column. 172 g (86% of theory) of pure 5-methylbutyrolactone of boiling point 65°–67° C./10 mbar were obtained.

EXAMPLE 7

228 g (2.0 moles) of methyl 2-trans-pentenoate, 9 g (0.5 mole) of water and 24 g of concentrated sulfuric acid (11.7 mol %, based on pentenoic ester) were initially taken in a 0.5 l three-necked flask having a 50 cm packed column and were heated at the boil (about 120°–130° C.). Thereafter, the remaining water (27 g, 1.5 moles) was added in the course of 4 hours, the methanol formed during the reaction being distilled off continuously. After all the methanol had been distilled off, the reaction mixture was stirred for a further 6 hours at a bottom temperature of 200° C. and then distilled over a short Vigreux column. 162 g (81% of theory) of pure 5-methylbutyrolactone of boiling point 65°–67° C./10 mbar were obtained.

EXAMPLE 8

228 g (2.0 moles) of methyl 2-cis-pentenoate, 9 g (0.5 mole) of water and 24 g of concentrated sulfuric acid (11.7 mol %, based on pentenoic ester) were initially taken in a 0.5 l three-necked flask having a 50 cm packed column and were heated at the boil (about 120°–130° C.). Thereafter, the remaining water (27 g, 1.5 moles) was added in the course of 1 hour, the methanol formed during the reaction being distilled off continuously. After all the methanol had been distilled off, the reaction mixture was stirred for a further 1 hour at a bottom temperature of 200° C. and then distilled over a short Vigreux column. 132 g (66% of theory) of pure 5-methylbutyrolactone of boiling point 65°–67° C./10 mbar were obtained.

EXAMPLE 9

228 g (2.0 moles) of methyl pentenoate (isomer mixture; about 20% by weight of methyl 4-pentenoate, 50% by weight of methyl 3-trans-pentenoate, 20% by weight of methyl 3-cis-pentenoate and 10% by weight of methyl 2-trans-pentenoate), 9 g (0.5 mole) of water and 24 g of concentrated sulfuric acid (11.7 mol %, based on pentenoate) were initially taken in a 0.5 l three-necked flask having a 50 cm packed column and were heated at the boil (about 120°–130° C.). Thereafter, the remaining water (27 g, 1.5 moles) was added in the course of 1 hour, the methanol formed during the reaction being distilled off continuously. After all the methanol had been distilled off, the reaction mixture was stirred for a further 4 hours at a bottom temperature of 200° C. and then distilled over a short Vigreux column. 176 g (88% of theory) of pure 5-methylbutyrolactone of boiling point 60°–67° C./10 mbar were obtained.

EXAMPLE 10

114 g (1.0 mole) of methyl 4-pentenoate and 189 g (10 moles) of water were refluxed together with 20 g of an acidic ion exchanger (DOWEX 50 Wx8, commercial product from Aldrich-Chemie, Steinheim), and the methanol formed was distilled off continuously. After 12 hours, the mixture was cooled, the ion exchanger was filtered off and the filtrate was distilled. 96 g (96% of theory) of pure 4-pentenoic acid of boiling point 55° C./2 mbar were obtained.

50 g (0.5 mole) of the 4-pentenoic acid thus obtained were heated to 180° C., 0.5 g of concentrated sulfuric acid (1 mol %, based on pentenoic acid) was added and the mixture was stirred for 1 hour at 180° C. and then distilled. 46 g (92% of theory) of pure 5-methylbutyrolactone of boiling point 65°–67° C. were obtained.

EXAMPLE 11

A mixture of 114 g (1.0 mole) of methyl 3-pentenoate (cis/trans isomer mixture, about 70% of methyl 3-transpentenoate and 30% of methyl 3-cis-pentenoate), 180 g (10 moles) of water and 20 g of a strongly acidic ion exchanger (DOWEX 50 Wx8) was refluxed, and the methanol formed was distilled off continuously. After 12 hours, the mixture was cooled, the ion exchanger was filtered off and the filtrate was distilled. 96 g (96% of theory) of pure 3-cis/trans-pentenoic acid of boiling point 107°–108° C./50 mbar were obtained.

50 g (0.5 mole) of the 3-cis/trans-pentenoic acid thus obtained were heated to 180° C., 0.5 g of concentrated sulfuric acid (1 mol %, based on pentenoic acid) was added and the mixture was stirred for 1 hour at 180° C. and then distilled. 46 g (92% of theory) of pure 5-methylbutyrolactone of boiling point 65°–67° C. were obtained.

EXAMPLE 12

A mixture of 114 g (1.0 mole) of methyl 2-trans-pentenoate, 180 g (10 moles) of water and 20 g of a strongly acidic ion exchanger (DOWEX 50 Wx8) was refluxed, and the methanol formed was distilled off continuously. After 150 hours, the mixture was cooled, the ion exchanger was filtered off and the filtrate was distilled. 73 g (73% of theory) of pure 2-trans-pentenoic acid of boiling point 55° C./2 mbar were obtained.

50 g (0.5 mole) of the 2-trans-pentenoic acid thus obtained were heated to 180° C., 0.5 g of concentrated sulfuric acid (1 mol %, based on pentenoic acid) was added and the mixture was stirred for 1 hour at 180° C. and then distilled. 46 g (92% of theory) of pure 5-methylbutyrolactone of boiling point 65°–67° C. were obtained.

EXAMPLE 13

A mixture of 1,500 g (13.1 moles) of methyl 3-pentenoate (cis/trans isomer mixture, about 70% of methyl 3-trans-pentenoate and 30% of methyl 3-cis-pentenoate), 2,960 g (164 moles) of water and 200 g of a strongly acidic ion exchanger (DOWEX 50 Wx8) was refluxed, and the methanol formed was distilled off continuously. After 20 hours, the mixture was cooled, the ion exchanger was filtered off and the filtrate was extracted with tertbutyl methyl ether. After the ether had been evaporated off, 1,260 g (96% of theory) of pure 3-cis/-trans-pentenoic acid were obtained.

1,260 g (12.6 moles) of the 3-cis/trans-pentenoic acid thus obtained were heated to 180° C., 12.5 g of concentrated sulfuric acid (1 mol %, based on pentenoic acid) were added and the mixture was stirred for 1 hour at 180° C. and then distilled. 2,212 g (96% of theory) of pure 5-methylbutyrolactone of boiling point 65°–67° C. were obtained.

We claim:

1. A process for preparing 5-methylbutyrolactone which comprises: reacting a pentenoic ester of the formula I $$X-CO_2R \qquad (I)$$

where X is $CH_2=CH-CH_2-CH_2-$, $CH_3-CH=CH-CH_2-$ or $CH_3-CH_2-CH=CH-$ and R is alkyl, cycloalkyl, aralkyl or aryl, or a mixture of these esters with water in the gas phase over a zeolite and/or phosphate catalyst, condensing the gaseous reactant products, separating the aqueous and organic phases and isolating 5-methylbutyrolactone from the reaction mixture.

2. The process of claim 1, wherein the pentenoic ester used in an alkyl pentenoate of 1 to 6 carbon atoms.

3. The process of claim 1, wherein from 1.0 to 10 moles of water are used per mole of pentenoic ester.

4. The process of claim 1, wherein the catalyst used is a zeolite of the pentasil type.

5. The process of claim 1, wherein the catalyst used is an aluminosilicate zeolite of the pentasil or faujasite type.

6. The process of claim 1, wherein the catalyst used is a phosphate of the elements boron, aluminum, cerium, zirconium, iron or strontium or a mixture of these.

7. The process of claim 1, wherein a phosphate prepared hydrothermally or by precipitation is used as the catalyst.

8. The process of claim 1, wherein the catalyst used is a precipitated boron phosphate.

9. The process of claim 1, wherein the reaction is carried out in the presence of an alcohol of 1 to 6 carbon atoms.

* * * * *